(12) United States Patent
Beck et al.

(10) Patent No.: US 6,639,660 B1
(45) Date of Patent: Oct. 28, 2003

(54) METHOD FOR MARKING AT LEAST ONE POINT ON AN OBJECT

(75) Inventors: Rainer Beck, Pliezhausen (DE); Sven Blickle, Sindelfingen (DE); Hans Ramsperger, Rottenburg (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 09/293,863

(22) Filed: Apr. 16, 1999

(30) Foreign Application Priority Data

Apr. 17, 1998 (DE) .......................... 198 16 992

(51) Int. Cl.⁷ .............................. G01N 21/00
(52) U.S. Cl. ................................ 356/237.2
(58) Field of Search .............. 356/375, 373, 356/237.1, 237.2, 237.3

(56) References Cited

U.S. PATENT DOCUMENTS

| | | | |
|---|---|---|---|
| 4,715,709 A | * 12/1987 | Sekine et al. | 356/237 |
| 5,248,878 A | 9/1993 | Ihara | 219/121.69 |
| 5,285,205 A | * 2/1994 | White | 340/932.2 |
| 5,606,647 A | 2/1997 | Hasebe | 395/107 |
| 5,663,806 A | * 9/1997 | Grise et al. | 358/406 |
| 6,013,308 A | * 1/2000 | Saito | 427/8 |

FOREIGN PATENT DOCUMENTS

| | | |
|---|---|---|
| DE | 3411578 A1 | 3/1984 |
| DE | 3418317 C1 | 5/1984 |
| DE | 3712513 C2 | 4/1987 |
| DE | 3737212 A1 | 11/1987 |
| DE | 38 08 119 A1 | 3/1988 |
| EP | 0 661 867 A2 | 2/1994 |
| EP | 0 729 806 A1 | 11/1994 |
| EP | 09241736 | 8/1997 |
| JP | 42448/1977 | 10/1975 |
| JP | 116382/1981 | 2/1980 |
| JP | 1780/1991 | 5/1989 |
| JP | 10-10054 | 1/1998 |
| JP | 11-064188 | 3/1999 |
| WO | PCT/GB/86/00399 | 11/1986 |
| WO | WO 98/53949 | 5/1998 |

* cited by examiner

*Primary Examiner*—Michael P. Stafira
(74) *Attorney, Agent, or Firm*—Kenyon & Kenyon

(57) ABSTRACT

Method for marking of at least one point on an object, especially for marking of at least one measurement point or a defect site on a vehicle or vehicle components, in which the object is illuminated with a light beam by means of at least one projection device, so that the point of impact of the light beam on the object defines the point being marked.

24 Claims, 1 Drawing Sheet

METHOD FOR MARKING AT LEAST ONE POINT ON AN OBJECT

BACKGROUND OF THE INVENTION

The present invention concerns a method according to the preamble of Patent claim 1.

It is sometimes necessary in vehicle manufacture to mark certain sites on the vehicle body or components. These can be measurement sites that are used to measure the auto body, or also defect sites that must be pointed out to an operating person.

Such sites are ordinarily marked by means of color markings, for example, chalk marks or entries in so-called error pictures or overview protocols. When markings are applied to painted surfaces, special caution must be exercised to avoid damage, for which reason manufacturing costs are increased. Chalk markings are also relatively nonpermanent and therefore poorly visible, whereas during marking with strongly adhering marking materials, it must be ensured that these do not attack the paint surfaces and are easy to remove again. On the other hand, the entry of measurement or error points in overview protocols must be carried out very carefully, which also leads to high work expense. The preparation of overview protocols also leads to a not insignificant labor demand, since the employed paper sheets must be ordered and managed.

A method for determining paint errors in vehicles is known from DE 34 11 578 A1, in which the paint surface is irradiated by a fluorescent tube, so that a mirror image of the fluorescent tube is produced by the paint surface. In addition to the mirror image of the fluorescent tube, the paint defects illuminated through the selected beam path must be recorded quantitatively with electro-optical devices. Actual evaluation occurs by means of CCD arrays with connected optics and must be considered very complicated. Marking of arbitrarily formed measurement points is not an object of this document and cannot be achieved with the method described there.

DE 34 18 317 C1 describes a test room for checking the surface of vehicle bodies, in which light rows are arranged above and beneath the body being checked. The bodies being checked are towed through the elongated test room. This layout is also not suitable for marking individual measurement points on a vehicle.

A surface test device for paint surfaces of vehicles is known from WO 87/00629, which evaluates laser light reflected on the paint surface. This type of evaluation requires high computer cost. Marking of specified points of the vehicle body is not an object of this document.

Finally, DE 37 12 513 C2 concerns a method for testing of an at least dull or shiny surface of a test piece for body defects, especially to check the surface of a painted vehicle surface for paint defects, and an apparatus for execution of this method. The body is illuminated here with diffuse light from a fixed light source to generate a light band on its surface. This type of method is unsuitable for marking individual points on a vehicle.

The task of the invention is therefore the preparation of a method, through which marking of individual sites or points on the surface of an object is simplified relative to the usual methods.

This task is solved by a method with the features of Patent claim 1.

According to the invention, a method is now made available which permits very simple and inexpensive marking of measurement points or defect sites on vehicles. The method is independent of material and poses no problems in conjunction with application and possibly removal of marking materials. Since no overview protocol must be kept, the writing and paper costs, as well as processing expense, are substantially reduced.

Advantageous embodiments of the method according to the invention are the object of subclaims connected to the main claim.

SUMMARY OF THE INVENTION

A laser or laser scanner is used advantageously as projection device. Points can be fixed precisely on the surface by means of a laser in very simple fashion, so that, for example, spacings between two or more such points can be determined with high precision. Because of this, vehicle bodies are very precisely measurable, for example, during production or also after accidents. According to a particularly preferred embodiment of the method according to the invention, a projection device is tracked according to a movement of the object, especially transport of a vehicle in a production line, to maintain the marking of at least one point. Tracking can occur here by means of a pivoting movement or a linear movement along the production line. By direct co-moving illumination or marking of the corresponding point, it is possible to mark the points over a specified zone in an ergonomically optimal method for an operating person. Control of the projection device expediently occurs via a measurement system computer. Information, especially concerning measurement results or defect sites, is displayed advantageously by projection directly onto the object. Symbol and/or color codes are offered for this purpose, which can also be projected by means of a projection device onto the object, especially a vehicle or a vehicle component.

BRIEF DESCRIPTION OF THE DRAWINGS

Preferred variants of the method according to the invention are now illustrated separately with reference to the drawing. In the drawing.

DETAILED DESCRIPTION OF PREFERRED EMBODIMENTS OF THE INVENTION

Figure 1:
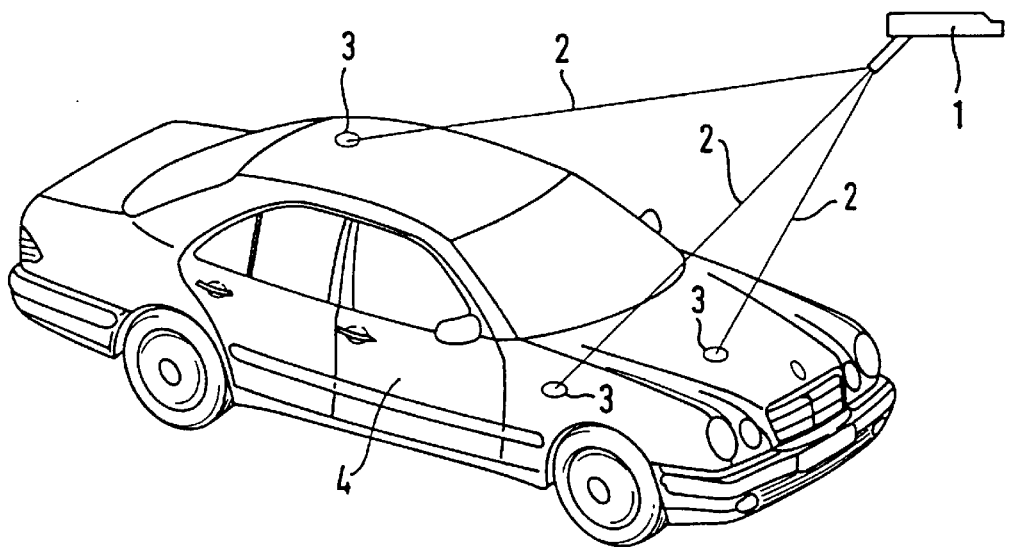
FIG. 1 schematically depicts use of the method according to the invention on the example of a stationary vehicle, and FIG. 2 schematically depicts use of the method according to the invention on the example of a vehicle transported on a production line.

A projection device 1 that projects light beams 2 onto a vehicle 4 is shown in FIG. 1. A laser or laser scanner is particularly preferred as projection device 1, which emits light of an appropriate visible wavelength.

Measurement or defect sites 3 are marked clearly and readily visible to an operating person by means of the light beams 2 on vehicle 4. For example, it is possible in a simple manner by means of a triangulation method to determine spacings between individual points for measurement of the vehicle body. The projection device 1 can be designed so that a number of measurement or defect sites 3 are illuminated simultaneously. However, it is also conceivable to provide successive illumination of the measurement or defect sites 3. For this purpose, the projector is pivoted or moved appropriately, for example, computer controlled. Establishment of the corresponding sites can occur controlled by a display screen, for example, in which the sites being marked are moved by means of a mouse on a monitor, on which the vehicle 4 or vehicle part is displayed (tracking system). The coordinates defined in this case are then sent to a control device, for example, a measurement system computer of projector 1, which initiates corresponding movement of projector 1. Direct input of coordinates (for example, angle of rotation and/or Cartesian coordinates) are also conceivable to control the projection device 1. It is also possible to project symbol or color codes or sketches onto the vehicle for direct display of measurement results on vehicle 4 by means of the projection device 1 or another projector 1. The corresponding measurements or markings can be coordinated by means of a CAD system and/or code numbers (not shown) to corresponding components.

Figure 2:
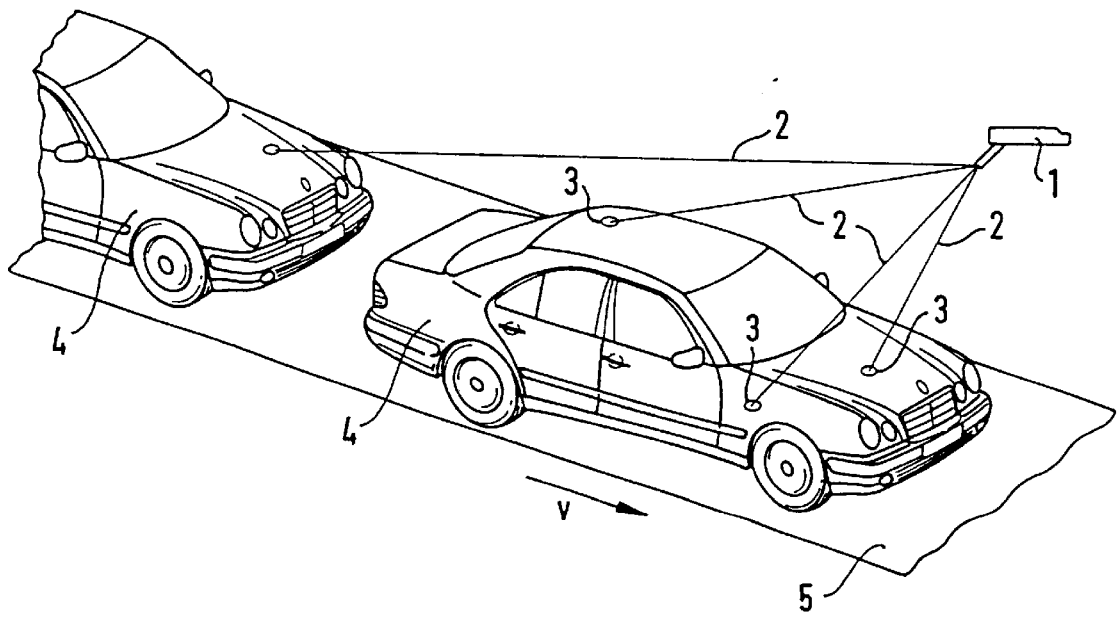

FIG. 2 shows another embodiment of the method according to the invention. Here the vehicle 4 being marked is positioned on a production line 5, which has a conveyor speed v. The projection device 1 can be controlled or pivoted or moved here, so that the markings of the defect or measurement sites 3 move with the vehicle 4.

Although the invention has been described in detail with reference to certain preferred embodiments and specific examples, variations and modifications exist within the scope and spirit of the invention as defined in the following claims.

What is claimed is:

1. A method for marking a plurality of fixed points on an object, comprising the steps of:
    illuminating the fixed points on the object with a laser having a light beam so that the impact of the laser's light beam defines the fixed point being marked; and
    determining a spacing between the illuminated fixed points.

2. The method according to claim 1 wherein the step of illuminating the object with a laser comprises illuminating the object with a laser scanner.

3. The method according to claim 1 wherein the point being marked comprises at least one of a measurement point and a defect site.

4. The method according to claim 1 wherein the object moves and the step of illuminating the object with the laser includes the step of tracking the movement of the object with the laser to maintain the marking of the at least one point on the object as the object moves.

5. The method according to claim 4 wherein the object comprises a vehicle being manufactured as it is transported on a production line.

6. The method according to claim 1 wherein the step of illuminating the object with the laser includes displaying information on the object using the laser.

7. The method according to claim 6 wherein the step of displaying information on the object comprises displaying information about measurement results on the object.

8. The method according to claim 6 wherein the step of displaying information on the object comprises displaying information about defect sites on the object.

9. The method according to claim 6, wherein the step of displaying information on the object comprises displaying informative symbols on the object.

10. The method according to claim 6 wherein the step of displaying information on the object comprises displaying color codes on the object.

11. The method according to claim 3 wherein the object comprises a vehicle being transported on a production line, the step of illuminating the object with the laser including the step of tracking the laser with the movement of the vehicle to maintain the marking of the at least one point on the vehicle as the vehicle is transported on the production line.

12. The method according to claim 11 and further including the step of displaying information on the vehicle with the laser.

13. The method according to claim 12 wherein the step of displaying information on the vehicle with the laser includes displaying information about defect sites on the vehicle.

14. The method according to claim 12 wherein the step of displaying information on the vehicle with the laser includes displaying information about measurement results on the vehicle.

15. The method according to claim 12 wherein the step of displaying information on the vehicle comprises displaying informative symbols on the vehicle.

16. The method according to claim 12 wherein the step of displaying information on the vehicle comprises displaying color codes on the vehicle.

17. A method of displaying information pertaining to a vehicle being manufactured as it is transported on a production line, comprising the steps of:
    determining the information in accordance with measurement of spacing between measurement points; and
    projecting the information onto the vehicle with one of a laser and a laser scanner and tracking the vehicle with the one of the laser and the laser scanner as the vehicle is transported on the production line to maintain the display of information on the vehicle as it is transported on the production line.

18. The method according to claim 17 wherein the step of projecting information onto the vehicle includes projecting information pertaining to one or more of measurement results and defect sites onto the vehicle.

19. A method of non-destructively marking at least one of measurement points and defect points on a vehicle being manufactured as it is transported on a production line, comprising the steps of:
    illuminating the points on the vehicle with a light beam of one of a laser and a laser scanner and tracking the movement of the vehicle as it is being transported on the production line with the one of the laser and the laser scanner to maintain the illumination of the point with the light beam as the vehicle is being transported on the production line; and
    determining a spacing between the illuminated points.

20. The method according to claim 19 and further including the step of displaying on the vehicle with the light beam of the laser information about the vehicle and the step of tracking the movement of the vehicle as it is being transported on the production line with the laser to maintain the illumination of the point with the laser's light beam also includes maintaining the display of information about the vehicle on the vehicle as it is being transported on the production line.

21. The method according to claim 20 wherein the information about the vehicle comprises measurement results.

22. The method according to claim 20 wherein the information about the vehicle comprises information about at least one defect site.

23. The method according to claim 20 wherein the step of displaying information on the vehicle comprises displaying informative symbols on the vehicle.

24. The method according to claim 20 wherein the step of displaying information on the vehicle comprises displaying color codes on the vehicle.

* * * * *